United States Patent [19]
Winslow et al.

[11] Patent Number: 5,400,137
[45] Date of Patent: Mar. 21, 1995

[54] PHOTOMETRIC MEANS FOR MONITORING SOLIDS AND FLUORESCENT MATERIAL IN WASTE WATER USING A STABILIZED POOL WATER SAMPLER

[75] Inventors: Gregory A. Winslow, Houston; Dale F. Brost, Sugar Land; Judith A. Newton, Houston, all of Tex.

[73] Assignee: Texaco Inc., White Plains, N.Y.

[21] Appl. No.: 104,704

[22] Filed: Aug. 11, 1993

[51] Int. Cl.⁶ ............................................. G01J 3/30
[52] U.S. Cl. ..................................... 356/318; 356/73; 250/435
[58] Field of Search ................ 356/73, 246, 317, 318, 356/338, 339, 417; 250/576, 428, 432 R, 434, 435

[56] References Cited
U.S. PATENT DOCUMENTS
| | | | |
|---|---|---|---|
| 3,306,157 | 2/1967 | Hach | 356/442 |
| 4,730,922 | 3/1988 | Bach et al. | 356/328 |
| 5,260,764 | 11/1993 | Fukuda et al. | 356/73 |

*Primary Examiner*—F. L. Evans
*Assistant Examiner*—Robert Kim
*Attorney, Agent, or Firm*—Kenneth R. Priem; James L. Bailey

[57] ABSTRACT

Turbidity and fluorescence measurements are taken simultaneously from a waste water sample in a stabilized pool of water in order to determine both the amount of solids and the amount of fluorescent material contained therein.

17 Claims, 2 Drawing Sheets

PHOTOMETRIC MEANS FOR MONITORING SOLIDS AND FLUORESCENT MATERIAL IN WASTE WATER USING A STABILIZED POOL WATER SAMPLER

BACKGROUND OF THE INVENTION

1. The Field of the Invention

The present invention relates to a method and apparatus for monitoring the concentration of solids and fluorescent materials in waste water. In particular, the present invention involves the combined use of surface fluorescence and surface turbidity measurements to determine the concentration of suspended/dispersed solids and dissolved and dispersed fluorescent materials in waste water.

2. The Prior Art

Waste water streams contain residual components whose discharge is controlled by government regulation. When waste waters are discharged into the environment, various government regulations require monitoring of the discharged water for contaminants, in particular for the solid and organic content. The results of such monitoring must be kept on file for government review. Depending of the type of waste water discharge, severe fines can be assessed when contaminate levels exceed maximum permissible limits. In an effort to comply with government regulations, industries involved with waste water discharge have been searching desperately for analytical instruments that can measure water quality in real time. Real time measurements could then be used to prevent illegal discharges by providing early warnings of excessive contaminant levels.

Fluorescence is indicative of various contaminants whose presence is not desirable in discharged water streams. Turbidity is a measure of suspended particles in a water stream (whether due to organic or inorganic materials) and is a measure of water quality. The present invention involves using a single instrument to simultaneously measure the fluorescence and turbidity of a water stream to determine the water quality of that stream. Although this invention would be very useful in monitoring water discharge streams from petroleum production, it would also be useful to monitor any sort of water stream. A variety of instruments and methods have been tested for their ability to continuously monitor solids and fluorescent materials in various waste water streams. The following discussion emphasizes the prior art in the area of monitoring residual oil in water streams resulting from petroleum production, but the present invention is not so limited.

Focused ultra-sonic beams have been used to determine the particle content and particle size distribution of suspended solids in water streams. This technique is incapable of detecting dissolved fluorescent materials and cannot distinguish between, for example, dispersed oil particles and other types of suspended solids of similar size.

Optical methods, based on turbidity (light scattering), absorption, and fluorescence, have also been applied. Turbidimetry can indicate the suspended particle content of a water stream, by sensing light that is scattered from the particles as, for example, described in U.S. Pat. No. 3,309,956. Like the ultra-sonic technique, this method can only give a measurement of total particle content and cannot distinguish between dispersed hydrocarbons and other types of suspended particles.

Absorption methods are based on the ability of aromatic hydrocarbons to absorb ultraviolet (UV) light in a manner that is proportional to concentration. These absorption methods are primarily useful for determining ppm levels of dissolved aromatic hydrocarbons. Total dissolved hydrocarbons can be estimated if the aliphatic hydrocarbons, which do not absorb in the UV range, are in constant proportion to the UV absorbing aromatic hydrocarbons. Absorption techniques can also monitor dispersed hydrocarbons, but only if all the dispersed particles can be assumed to be 100% oil and if the particle size distribution is constant. Hybrid instruments are available which are capable of simultaneous absorption and turbidity measurements.

Fluorescence instruments also detect the aromatic components of petroleum hydrocarbons, but at much lower concentrations (parts-per-billion) than absorption instruments. Successful application of the fluorescence technique depends upon the same assumptions as discussed above for the absorption technique. The present invention combines the techniques of turbidimetry and fluorescence into one water monitoring instrument that is not subject to fouling of the optical surfaces by contact with the water stream.

All the optical measurement techniques require a means for light to come into contact with the water, and for transmitted, scattered, or fluorescent light to be detected. A variety of flow cells with optical windows or fiber optic probes are available for this purpose. The optical windows of flow cells and fiber optic probes are subject to fouling in most waste water streams because the suspended particles in the system (hydrocarbons, bacteria, etc.) cling to the optical surfaces and interfere with the transmission of light.

For fluorescence and turbidity measurements, non-contact sample cells are also available. Light is directed through open space to either a falling stream of water or a stabilized flowing water surface. Scattered or fluorescent light is then directed through an open space to a light detector. Fouling is eliminated because there is no direct contact between the water sample and the optical surfaces. One example of this optical arrangement is the Surface Scatter 6 Turbidimeter, described in the above mentioned U.S. Pat. No. 3,309,956, for the measurement of highly turbid samples.

An example of the falling stream system for the measurement of fluorescence is an instrument manufactured by Sigrist (Sigrist, Ennetburgen, Switzerland). An example of the falling stream system for the measurement of turbidity is also made by Sigrist.

In the prior art there are many examples of photometers, but only one is found that is capable of measuring absorbance, turbidity, nephelometric light, and fluorescence at the same time. There are no known examples of photometers which can make more than one type of measurement and are able to correct the fluorescence reading for error due to turbidity of the sample, or which use a sample cell that will not be easily fouled by a waste water stream.

U.S. Pat. No. 4,060,327 shows a device which is capable of measuring only absorbance and turbidity. It also uses a sample cell which would be susceptible to fouling in a waste water stream.

The system described in U.S. Pat. No. 4,426,154 is a device which measures fluorescent light, scattered light, and/or absorbed light, however it cannot measure nephelometric light.

Baker Instruments has a system which is capable of both absorbance and fluorescence measurements, but not nephelometric measurements.

U.S. Pat. No. 4,730,922 describes an instrument which is capable of measuring fluorescence, turbidity, absorbance, and nephelometry. However, a very crucial part of that instrument is the sample cell which would be very easily fouled by a waste water stream. Also, that invention does not seem to have the capability to correct the fluorescence measurement for the effects of turbidity.

SUMMARY OF THE INVENTION

The present invention uses a non-contact optical arrangement for simultaneously measuring fluorescence and turbidity in a single instrument. The optical arrangement is based upon a stabilized pool water sampler in which light beams travel to and from the water sample without ever passing through an optical material in physical contact with the water sample. The subject instrument also has means for correcting the fluorescence reading for the effect of turbidity.

BRIEF DESCRIPTION OF THE DRAWINGS

The present invention will now be described, by way of example, with reference to the accompanying drawings in which.

DESCRIPTION OF THE PREFERRED EMBODIMENT

Figure 1:
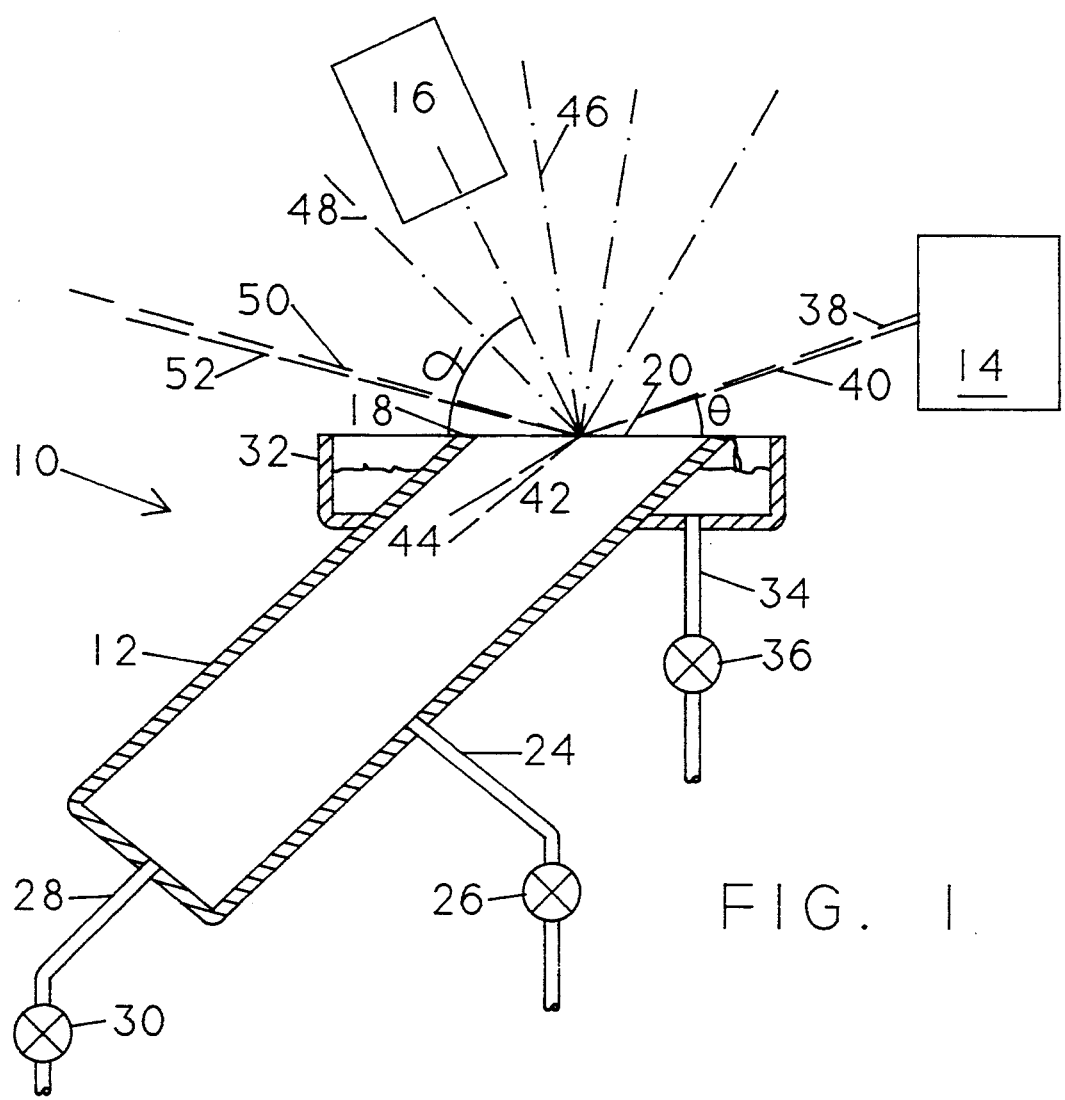
FIG. 1 is a schematic side elevation of one embodiment of the present invention.

FIG. 1 schematically shows a non-contact optical arrangement of the present invention using a stabilized pool water sampler as the basis of an instrument which is capable of performing simultaneous fluorescence and turbidity measurements. The device 10 has a fluid sample container 12, a dual beam light source 14, and a light sensing detector 16. The fluid sample container 12 has an open upper end formed by a horizontal edge 18 defining sample surface 20. The sample fluid is fed to the container 12 through inlet 24 which is connected to a source (not shown) and controlled by valve 26. The inlet 24 is sufficiently spaced below the surface 20 to prevent any turbulence from the inflow from affecting the surface 20. A bottom drain 28 controlled by valve 30 provides means to clean out excess heavy solids that settle to the bottom of container 12 during normal operation. The upper end of the container 12 is surrounded by a catch basin 32 to catch the fluid flowing over the edge 18. The catch basin 32 has a drain 34, controlled by valve 36, connected to suitably dispose of the sample fluid or return it to its original source.

A water stream is brought at constant velocity into the center of a fluid sample container 12. The water rises to the top and overflows the horizontal edge 18 into catch basin 32. This forms an optically smooth surface (stabilized pool) 20.

The dual-wavelength light source 14 emits two beams of light, 38 and 40 incident at an acute angle $\Theta$ on the same target portion of the stabilized pool surface 20. Beam 38 has a wavelength in the ultraviolet or visible portion of the spectrum that stimulates fluorescent emissions, for example, from dissolved and dispersed fluorescent materials in the water stream. Beam 40 has a wavelength in the visible or infrared portion of the spectrum, which is so selected that it does not stimulate fluorescent emissions, but rather is scattered by the suspended particles dispersed in the water system. Fluorescent emissions are stimulated at the surface of the water by incident beam 38 and below the water surface by refracted beam 42. Likewise, incident beam 40 is scattered by particles at the water surface and refracted beam 44 is scattered by particles below the surface. Both the fluorescent emissions stimulated by beams 38 and 42 and the scattered portions of beams 40 and 44 emerge from the water at all angles 46, 48 above the surface 20 of the stabilized pool. Both the fluorescent emissions and the scattered light are selectively detected by detector 16 which is placed above the water surface at some angle $\alpha$, which is not equal to angle $\Theta$. Angle $\alpha$ is not equal to angle $\Theta$ to prevent reflected beams 50 and 52 from entering detector 16.

Fluorescent and scattered light can be separately detected using either time-division or frequency multiplexing, both of which are techniques well known in the art. With either technique, detector 16 would be configured so that it would not detect the wavelength used in beam 38, but would be sensitive to both the fluorescent wavelengths stimulated by beam 38 and scattered light at the wavelength of beam 40. When using time-division multiplexing, beams 38 and 40 would be alternated in time, so that only one beam hits the water surface at any given time. When beam 38 is incident on the sample, the signal from detector 16 is proportional to the fluorescent light intensity emitted by the sample. When beam 40 is incident on the sample, the signal from detector 16 is proportional to the amount of beam 40 that is scattered into detector 16 by the sample. As an example of one type of frequency multiplexing, beams 38 and 40 would be simultaneously incident on the sample surface, but would be modulated at different frequencies. To selectively detect fluorescent emissions, the signal from detector 16 would be demodulated at the frequency of beam 38, using, for example, a lock-in amplifier tuned to the frequency of beam 38. To selectively detect scattered light, the signal from detector 16 would be demodulated at the frequency of beam 40. Many other known frequency multiplexing techniques could also be used to separately detect the fluorescent emissions and scattered light.

The present invention could also be configured with many other incident beam/detector arrangements including, but not limited to: 1) a single dual-wavelength beam and a single multi-wavelength detector; 2) a single dual-wavelength beam with two separate detectors; 3) two single-wavelength beams with two separate detectors, etc. All of these optical arrangements are well known in the art.

The intensity of the scattered light resulting from beam 40 is a function of the suspended particle content of the water sample. The intensity of the fluorescent light resulting from beam 38 is a function primarily of the fluorescent material concentration of the sample. The measured light intensities are mathematically combined with appropriate calibration constants to determine the solids and fluorescent materials content of the water stream.

Figure 2:
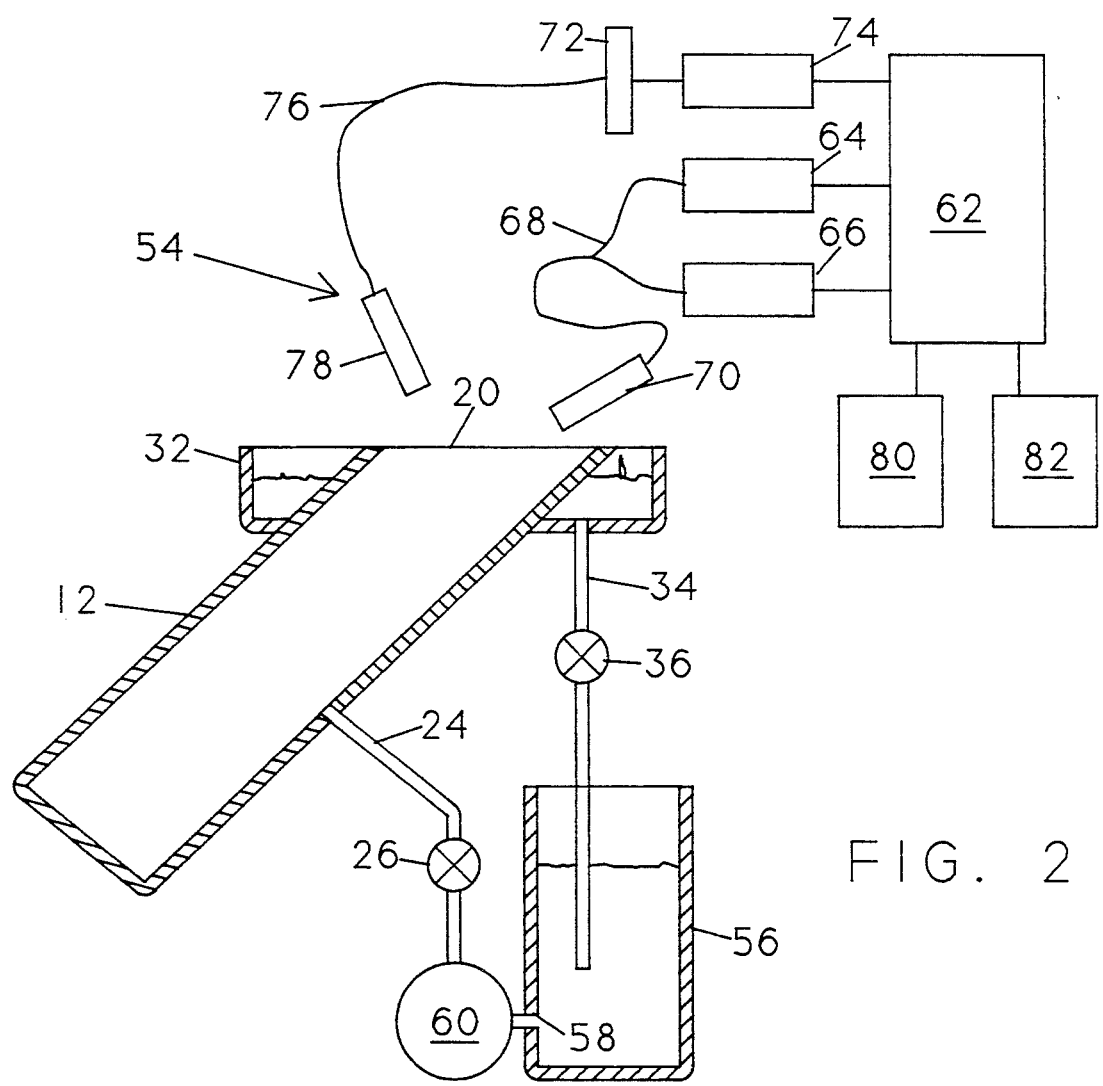
FIG. 2 is a schematic side elevation of a laboratory apparatus used to evaluate the performance of the present invention.

A test instrument 54 was constructed as illustrated in FIG. 2 and incorporating the present invention. The sample fluid container 12 was substantially identical to that previously described so like reference numerals have been used to identify like parts. The major difference is drain 34 feeds into container 56 which is connected by pipe 58 to pump 60 which is connected to input line 24 to form a closed fluid loop. A dual-wavelength, time-division multiplexing, fiber optic photometer 62 was used to supply the two incident light beams and to detect the fluorescent and scattered light emerging from the sample. Light beam 1 from source 64 (fluorescence excitation) had a wavelength of 490 nm. Light beam 2 from source 66 (light scattering) had a wavelength of 600 nm. Both light sources were connected to a bifurcated fiber optic cable 68 connected to probe 70. A long-pass filter 72 with a cut-on wavelength of 515 nm was placed in front of the photometer's photomultiplier detector 74 and connected by fiber optic cable 76 to probe 78. The pump 60 was used to continuously circulate a fixed volume of deionized water through the stabilized pool system 12. Fluorescence and turbidity (scattering) responses were measured as various chemical substances were added to the circulating water.

To investigate the instrument's response to fluorescence in the absence of turbidity, fluorescence response was measured as known aliquots of PYLA-TEL Fluorescent Yellow dye (Pylam, Garden City, N.Y.) were successively added to the circulating water. A calibration curve was constructed by plotting dye concentration versus fluorescence response. The resulting curve was linear from 0 to 0.22 ppm and had an intercept of zero. A linear least squares fit through the measured data gave a correlation coefficient (R squared) of 0.9997.

In another experiment, the instrument's turbidity response was measured in the absence of fluorescence. Aliquots of barium chloride were successively added to the circulating water, which contained an excess of sodium sulfate. This resulted in the formation of increasing levels of suspended barium sulfate particles. After each barium chloride addition, a small sample was removed and its turbidity was measured with a laboratory turbidimeter (Ratio XR Turbidimeter, HACH Company, Loveland, CO). A calibration curve was constructed by plotting the measured turbidity of the sample versus the test instrument's turbidity response. The resulting calibration curve was linear from 0 to 325 NTU and had an intercept of zero. A linear least squares fit through the measured data gave a correlation coefficient (R squared) of 0.99.

Another experiment was carried out to determine the effect of sample fluorescence on turbidity response. Barium chloride was added to a circulating sodium sulfate solution to give a barium sulfate turbidity of 325 NTU (as determined with the laboratory turbidimeter). Fluorescence was then added stepwise by adding successive aliquots of PYLA-TEL Fluorescent Yellow dye to the circulating solution. The final dye concentration was 0.22 ppm, which gave a strong greenish yellow color to the solution and resulted in a very strong fluorescence response. Results showed that the turbidity response was completely independent of added dye over the dye concentration investigated.

A final experiment was carried out to determine the effect of sample turbidity on fluorescence response. A deionized water sample was made fluorescent by the addition of PYLA-TEL Fluorescent Yellow dye. Dye concentration was 0.22 ppm, which gave a strong fluorescence response. An excess of sodium sulfate was added to the fluorescent solution. Aliquots of barium chloride were then added successively, to produce varying degrees of barium sulfate turbidity. After each aliquot, a sample was taken and the turbidity was measured with the laboratory turbidimeter. Results showed that fluorescence response increased by 9.0% as turbidity increased from 0 to 324 NTU. A plot of fluorescence response versus turbidity response showed that the turbidity effect could be fit with a second order polynomial. Subsequent experiments carried out in the same manner showed that the effect was repeatable, allowing the polynomial function to be used to quantitatively correct the fluorescence response for the presence of turbidity.

The preceding experiments show that the test instrument built according to this embodiment, gave linear response to both fluorescence and turbidity. The results also show that turbidity response was independent of fluorescence over the range investigated. Finally, the results show that turbidity had a small effect on fluorescence response, and that the turbidity response could be used to correct for this effect. The ability to correct fluorescence measurements for such turbidity effects is unknown in the prior art.

The present invention would be useful for the detection of many types of fluorescent materials which are foreign to pure water. These include, but are not limited to, aromatic hydrocarbons, corrosion inhibitors, pesticides, human or animal wastes, etc. The ability to correct fluorescence response for presence of turbidity, makes this invention especially suited to the analysis of optically dense and turbid water samples (e.g., river water containing silt, oil field waters containing dispersed suspended particles such as clays, iron sulfide, iron oxide, bacteria, etc.) The invention will also be useful for measuring turbidity from many sources including, but not limited to dispersed hydrocarbons, biomass, debris, and any other water insoluble but water dispersed materials.

The present invention is especially suited, but not limited to, the analysis of oil field waters, which often contain fluorescent dispersed hydrocarbons, as well as a wide variety of non-fluorescent suspended solids. It is often permitted to discharge oil field waters to natural water systems as long as the dispersed hydrocarbon content is low, even if the dispersed solids content is high. Both of these substances can be simultaneously determined by application of the present invention. Also, since the present invention is not susceptible to fouling, it provides a trouble-free means for reliable, long-term monitoring.

The present invention may be subject to many modifications and changes without departing from the spirit or essential character thereof. The present description should therefore be considered in all respects as being illustrative rather than restrictive of the scope of the invention.

We claim:

1. A method for monitoring the concentration of solids and fluorescent materials in waste water comprising the steps of:

forming an optically stabilized pool of water by allowing a moving stream of said water to overflow a horizontal upper end of a fluid container;

directing a first beam of light at said stabilized pool;

directing a second beam of light at said stabilized pool;

measuring fluorescent emission stimulated by said first beam of light; and measuring turbidity from the light scattered from said second beam of light whereby the fluorescence measurements are corrected for the effects of turbidity by utilizing a calculation of fluorescence versus turbidity.

2. A method according to claim 1 wherein said first beam of light is in the ultraviolet portion of the spectrum and said second beam of light is in the visible portion of the spectrum.

3. A method according to claim 1 wherein said first beam of light is in the visible portion of the spectrum and said second beam of light is in the infrared portion of the spectrum.

4. A method according to claim 1 wherein said first beam of light is in the visible portion of the spectrum and said second beam of light is in the visible portion of the spectrum.

5. A method according to claim 1 wherein said first beam of light is in the ultraviolet portion of the spectrum and said second beam of light is in the infrared portion of the spectrum.

6. A method according to claim 1 wherein said first beam is of a first wavelength range suitable for stimulating fluorescence from the water sample and said second beam is of a second wavelength range which does not stimulate significant fluorescence from the water sample but is suitable for scattering by the sample where the shortest wavelength of said second wavelength range is equal to or greater than the shortest fluorescence wavelength to be detected.

7. A method according to claim 1 wherein a single photodetector using time-division multiplexing separately detects fluorescent emission and scattered light.

8. A method according to claim 1 wherein a single photodetector using frequency multiplexing separately detects fluorescence emissions and scattered light.

9. A method according to claim 1 wherein a single multi-wavelength detector separately detects fluorescence emissions and scattered light.

10. A method of monitoring the concentration of solids and fluorescent material in water comprising the steps of:

directing a beam of light at a stabilized pool of water wherein said light beam is comprised of both a first wavelength range suitable for stimulating fluorescence from the water sample and a second wavelength range which does not stimulate significant fluorescence from the water sample but is suitable for scattering by the water sample where the shortest wavelength of said second wavelength range is equal to or greater than the shortest fluorescence wavelength to be detected; and a detector selectively monitors the intensity of said first and second wavelength ranges whereby both the fluorescence and turbidity of said waste water are measured so that said fluorescence measurements are corrected for the effects of turbidity by utilizing a calculation of fluorescence versus turbidity.

11. An apparatus for monitoring the concentration of solids and fluorescent material in waste water comprising:

means for establishing a sample surface of water to be measured;

means for generating and directing a first beam of light at said water sample surface;

means for generating and directing a second beam of light at said water sample surface;

means for detecting and measuring fluorescent emissions stimulated by-said first beam of light; and means for detecting and measuring the light scattered from said second beam of light whereby both fluorescence and turbidity of said waste water are measured so that the fluorescence measurements are corrected for the effects of turbidity by utilizing a calculation of fluorescence versus turbidity.

12. An apparatus according to claim 11 wherein said first beam of light is generated in the ultraviolet portion of the spectrum and said second beam of light is generated in the visible portion of the spectrum.

13. An apparatus according to claim 11 wherein said first beam of light is in the visible portion of the spectrum and said second beam of light is in the visible portion of the spectrum.

14. An apparatus according to claim 11 wherein said first beam of light is in the visible portion of the spectrum and said second beam of light is in the infrared portion of the spectrum.

15. An apparatus according to claim 11 wherein said first beam of light is in the ultraviolet portion of the spectrum and said second beam of light is in the infrared portion of the spectrum.

16. An apparatus according to claim 11 wherein said first beam is of a first wavelength range suitable for stimulating fluorescence from the water sample and said second beam is of a second wavelength range which does not stimulate significant fluorescence from the water sample but is suitable for scattering by the sample where the shortest wavelength of said second wavelength range is equal to or greater than the shortest fluorescence wavelength to be detected.

17. An apparatus according to claim 11 wherein said waste water is formed into a stabilized surface and said first and second beams of light are directed at said surface.

* * * * *